United States Patent [19]
Heinisch et al.

[11] Patent Number: 6,124,290
[45] Date of Patent: Sep. 26, 2000

[54] POLYCYCLIC PHTHALAZINE COMPOUNDS AND THEIR USE

[75] Inventors: Lothar Heinisch; Ute Moellmann, both of Jena; Wolfgang Witte, Elend; Christiane Cuny, Silstedt; Ernst Roemer, Bucha; Walter Werner; Udo Graefe, both of Jena, all of Germany

[73] Assignee: Gruenenthal GmbH, Aachen, Germany

[21] Appl. No.: 09/242,295

[22] PCT Filed: Jul. 9, 1997

[86] PCT No.: PCT/FI96/03632

§ 371 Date: Jan. 28, 2000

§ 102(e) Date: Jan. 28, 2000

[87] PCT Pub. No.: WO98/07706

PCT Pub. Date: Feb. 26, 1998

[30] Foreign Application Priority Data

Aug. 17, 1996 [DE] Germany .................. 196 33 221

[51] Int. Cl.[7] .................................................. A61K 31/435
[52] U.S. Cl. .......................................... 514/248; 544/233
[58] Field of Search ............................. 514/248; 544/233

[56] References Cited

PUBLICATIONS

Fleck et al., "Fermentation, Isolation, and Biological Activity of Maduramycin: A New Antibiotic from *Actinomadura rubra*", *Zeitschrift fur allgemeine Mikrobiologie* 18:389–398 (1978).

Paulus et al., "Madurahydroxylactone". *Acta Crystallographica* Section C C50:2064–67 (1994).

Oki, "A New Family of Antibiotics: Benzo[α] Naphthacenequinones". *Recent Progress in Antifungal Chemotherapy* 381–402 (1990).

Witte et al., "Analysis of Nosocomial Outbreaks with Multiply and Methicillin–Resistant *Staphylococcus aureus* (MRSA) in Germany: Implications for Hospital Hygiene". *Infection* 22:128–133 (1994).

Eliopoulos, "Increasing Problems in the Therapy of Enterococcal Infections". *Eur. J. Clin. Microbiol. Infect. Dis.* 12:409–412 (1993).

*Primary Examiner*—James Reamer
*Attorney, Agent, or Firm*—Evenson, Mckeown, Edwards & Lenahan, P.L.L.C.

[57] ABSTRACT

Polycyclic phthalazines, in particular 2-substituted maduraphthalazines (10,12,15,16-tetrahydroxy-8-methoxy-11-methyl-1,9,14-trioxo-1,2,6,7,9,14-hexahydronaphthaceno-1,2-g-phthalazines), of formula I and their use against gram-positive bacterial strains, particularly against multi-resistant staphylococci (MRSA) and against glycopeptide-resistant, for example vancomycin-resistant, enterococci. The polycyclic phthalazines are thus suitable for preparing antibacterially effective pharmaceutical compositions. In formula I, $R^1$ is carboxyalkyl or carboxyaryl, and $R^2$ and $R^3$ represent H or acyl (for example CO-alkyl or COO-alkyl), with $R^1$ being different from optionally substituted carboxyphenyl when $R^3$ represents $C_{1-8}$ alkanoyl. The invention also relates to salts, amides and esters of compounds of formula I.

12 Claims, No Drawings

POLYCYCLIC PHTHALAZINE COMPOUNDS AND THEIR USE

BACKGROUND OF THE INVENTION

This invention relates to new polycyclic phthalazine derivatives, particularly 2-carboxyalkyl- and 2-carboxyaryl-substituted maduraphthalazines (10,12,15,16-tetrahydroxy-8-methoxy-11-methyl-1,9,14-trioxo-1,2,6,7,9,14-hexahydronaphthaceno-[1,2-g]-phthalazines) as well is salts, esters and amides thereof. They constitute substances which exhibit a strong antibacterial effect against Staphylococci, particularly against gram-positive Staphylococci, and especially against multi-resistant Staphylococci (MRSA) and resistant Enterococci, and can be used for combatting infectious diseases in humans and animals. These compounds are suitable for the production of very different pharmaceutical preparations and forms of application.

The compounds are the first representatives of a hitherto unknown ring system, namely of naphthaceno-[1,2-g]-phthalazine. They are derived from madurahydroxylactone or maduranic acid, which can be obtained by a biotechnology route from *Actinomadura rubra* (W. Fleck, D. G. Strauss, J. Meyer, Z. Allg. Mikrobiol. 18, 368–398 (1978)). The structure of madurahydroxylactone (formula II) has been elucidated by Paulus and co-workers (E. F. Paulus, K. Dornberger, W. Werner, D. Fenske, Acta Cryst. (1994) C50, 2064–2067). Madurahydroxylactone itself only exhibits an unsatisfactory biological efficacy. Madurahydroxylactone forms part of the benzonaphthacenequinone class, from which benanomycins and pradimycins in particular have recently become known as antifungal substances of interest (T. Oki in "Recent Progress in Antifungal Chemotherapy", Eds. H. Yamaguchi, G. S. Kobayachi, H. Takahashi, Marcel Dekker, Inc., New York, Basle, Hong Kong, 1992, page 38).

SUMMARY OF THE INVENTION

The present invention serves to provide 2-substituted, particularly 2-carboxyalkyl- and 2-carboxyaryl-substituted, Maduraphthalazines (10,12,15,16-tetrahydroxy-8-methoxy-11-methyl-1,9,14-trioxo-1,2,6,7,9,14-hexahydro-naphthaceno-[1,2-g]-phthalazines) and the corresponding salts, esters and amides, and also relates to the use thereof. With these compounds, efforts have been made to increase the range of antibacterial preparations, especially preparations which are effective against grain-positive bacteria and which are effective against multi-resistant Staphylococci in particular. These new compounds are advantageous for the achievement of this object because the compounds or anti-infection preparations which were known hitherto possess serious disadvantages, such as insufficient effectiveness against super-resistant bacterial strains for example (W. Witte, C. Braulke, D. Heuck, C. Cuny; "Analysis of nosocomial outbreaks with multiple- and methicillin-resistant *Staphylococcus aureus* (MRSA) in Germany: implications for hospital hygiene", Infection 22, (1994), Suppl. 2, 128–134; G. M. Eliopulos, "Increasing problems in the therapy of enterococcal infection", Eur. J. Clin. microbiol. Infect. Dis. 12 (1993) 409–412.

This object is achieved according to the invention by the provision of new polycyclic phthalazine derivatives of general formula I

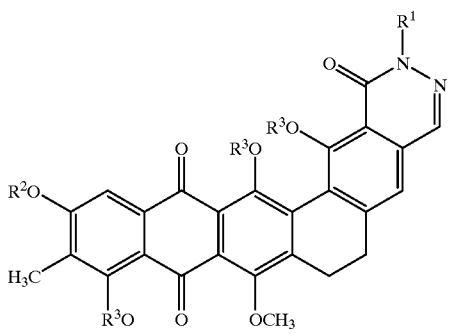

wherein $R^1$ denotes carboxyalkyl or carboxyaryl and $R^2$ and $R^3$, independently of each other, represent hydrogen or acyl, as well as salts, esters and amides of compounds of formula I, with the proviso that $R^1$ is different from a carboxyphenyl group, which is optionally substituted, if $R^3$ denotes $C_{1-8}$ alkanoyl.

Within the scope of the present invention, the term "alkyl" (in compound words also, such as alkoxy or carboxyalkyl) denotes a $C_{1-10}$ alkyl which may be a straight-chain or branched-chain alkyl, preferably a $C_{1-4}$ alkyl, whilst an aryl radical (including any one of the aryl radicals which are further cited below, or in compound words such as aralkyl) is to be understood to mean a substituted or unsubstituted aryl group, particularly a corresponding phenyl group, the substituents of which can be OH, O-alkyl, O-aryl, a halogen, alkyl or aryl. Within the scope of the present invention, the term "acyl" primarily means a $C_{1-8}$ alkanoyl, $C_{1-8}$ alkoxycarbonyl or aroyl group, particularly a benzoyl or a substituted benzoyl group (wherein the substituents are the same as for a substituted aryl), and optionally a carbamoyl group which is substituted by one or two $C_{1-4}$ alkyl radicals.

Examples of corresponding $R^1$ radicals are those of formulae $—(CR^4R^5)_n—COY$ or

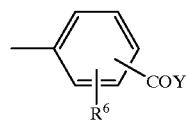

wherein $R^4$ and $R^5$=H, alkyl or aryl or a substituted aryl, n=1–4, $R^6$=H, alkyl, OH, alkoxy in the o-, m- or p-position or COY in the o-, m- or p-position, and Y=$OR^7$, wherein $R^7$=H, alkyl, aryl or a substituted aryl, an alkali metal ion, such as $Na^+$ or $K^+$ for example, or an ammonium ion ($NH_4^+$ or a mono-, di- or trialkylammonium ion or an N-methyl-D-glucammonium salt), or Y=$NR^8R^9$, wherein $R^8$ and/or $R^9$ can be H, alkyl, aryl or a substituted aryl or aralkyl. If asymmetric C atoms are present, the present invention also relates to the corresponding D- and L-forms, enantiomers and diastereoisomers, and also relates to racemates or mixtures of enantiomers and diastereoisomers.

DETAILED DESCRIPTION OF THE PREFERRED EMBODIMENTS

In the compounds of formula I which are particularly preferred, $R^1$ represents carboxy-$C_{1-4}$ alkyl or $C_{1-4}$ alkoxycarbonyl-$C_{1-4}$ alkyl or represents carboxyphenyl, and $R^2$ and $R^3$ represent hydrogen, wherein the carboxy group exists in its free form or in salt form. The compounds of formula I and the salts thereof which are cited in the examples should be emphasised.

The compounds according to the invention are prepared, for example, by the reaction of madurahydroxylactone or maduranic acid (3,9,11,14,15-pentahydroxy-10-methyl-7-methoxy-1,8,13-trioxo-1,3,5,6,8,13-hexahydro-naphthaceno-[1,2-f]-benzoisofurane) of formula II

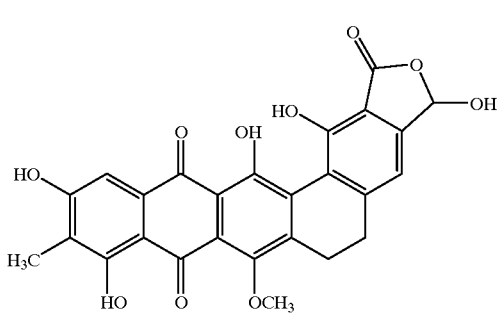

with hydrazinoalkylcarboxylic acids or hydrazinophenylcarboxylic acids or esters and amides thereof, optionally in the form of salts thereof. The reaction is conducted with the use of suitable solvents, e.g. glacial acetic acid. The temperature of reaction is usually the boiling temperature of the solvent, and the time of reaction can range from one to a few hours.

Compounds of formula I which are prepared according to the invention can be converted in the manner known in the art into other compounds of formula I. Compounds of formula I which can be obtained and wherein Y=O-alkyl can thus be converted into the corresponding acids (formula I wherein Y=OH) by alkaline saponification, e.g. with 2M caustic soda, and subsequent acidification, e.g. with 2M hydrochloric acid. Alternatively, compounds of formula I which are obtained and in which $R^2$ or $R^3$=H can be converted into O-acyl derivatives, corresponding to formula I with $R^2$ or $R^3$=H or acyl (e.g. —CO-alkyl or —COO-alkyl), by the acylation of the phenolic OH groups in a second step. This reaction step is conducted by employing customary methods for the acylation of phenolic OH groups, e.g. by means of an acid anhydride (e.g. acetic anhydride or propionic anhydride) or by means of esters of chloroformic acid (e.g. methyl chloroformate) in alkaline solution, e.g. in 2M caustic soda or in tetrahydrofuran/triethylamine. The reaction temperature can range from –20° C. to +20° C.

Compounds which are obtained in which Y=OH can be converted by customary methods into the corresponding salts in which Y=$OR^7$, wherein $R^7$ can be an alkali metal ion (e.g. Na, K) or an ammonium ion ($NH_4$, a mono-, di- or trialkylammonium ion, e.g. a triethylammonium ion or an N-methyl-D-glucammonium ion). The synthesised compounds can be purified by means of customary methods (e.g. by recrystallisation or column chromatography).

Compounds which are prepared according to the invention inhibit the growth of bacteria, particularly of gram-positive bacteria, especially of multi-resistant Staphylococcus and of Enterococci. An aspect of particular importance is that the compounds are also highly effective against quinolone-resistant Staphylococci and are also highly effective against multiply-resistant strains (MRSA), and are even highly effective against glycopeptide-resistant strains, e.g. against vancomycin-resistant hospital strains.

The minimum inhibiting concentration (MIC) of the compounds was tested, in a micro-broth dilution test according to DIN 58 940 (Part 8), against the following bacterial strains: *Staphylococcus aureus,* strains 8325-4 (a sensitive *Staphylococcus aureus* strain which is representative of the species), NCTC 6571 (a sensitive international control strain), 108/83 (an "old" MRSA without quinolone-resistance), 134/94 (a "new" MRSA, with quinolone-resistance), *Staphylococcus epidermidis* CCM 2124 (a sensitive control strain), *Enterococcus faecium* 70/90 (a vancomycin-resistant strain) and 64/3 (a sensitive strain). The known substances vancomycin, teicoplanin and ciprofloxacin were used for comparison in the tests, even though they are structurally different.

The results of the antibacterial testing are compared in the Table. It follows from the results that the substances which were prepared according to the invention exhibit inhibiting effects against some bacterial strains which are significantly superior to those of the comparison substances, and are capable of successfully overcoming bacterial resistance.

On account of their antibacterial properties, compounds of general formula I are suitable for use as drugs for bacterial infections, particularly infection by multi-resistant Staphylococci. For diseases such as these, compounds of formula I can be used either on their own or with physiologically compatible adjuvant substances or support substances, wherein all customary pharmacological forms of application and physiologically compatible dosages are possible in principle. Application is effected orally or parenterally for example, e.g. intravenously.

EXAMPLES

Example 1

Substance 1

2-(4-carboxyphenyl)-maduraphthalazine (2-(4-carboxyphenyl-10,12,15,16-tetrahydroxy-8-methoxy-11-methyl-1,9,14-trioxo-1,2,6,7,9,14-hexahydro-naphthaceno-[1,2 g]-phthalazine), formula I wherein $R^1$=4-carboxyphenyl, $R^2$, $R^3$=H, $C_{33}H_{22}N_2O_{10}$(606.54).

A mixture of 100 mg (0.2 mmoles) madurahydroxylactone (80 percent) and 50 mg 4-hydrazino-benzoic acid (0.2 mmoles) was boiled under reflux in 10 ml glacial acetic acid for 4 hours. The red crystals obtained were washed with ether.

The substance was purified twice via preparative DC (Merck ready-to-use 1 mm Si 60 plates, mobile phase $CH_2Cl_2/CH_3OH$ (9:1)), dissolved in THF, filtered and precipitated with petroleum ether. Yield 78 mg (63% theoretical), m.p.>350° C., purity as determined by HPLC (Eurospher, acetonitrile/water (3:2)): 94,7%, t=9.4 minutes, DC (Merck Alufolie Si 60), mobile phase $CH_2Cl_2/CH_3OH$ (9:1)), $R_f$=0.77,
MS FAB (3NBA) $[M+H]^+$: mass number found=607.1, $^1H$ NMR (DMSO-$D_6$): d (ppm)=14.1, 13.6, 12.98, 11.2 (4H, s, 10-,12-,15-,16-OH) 8.6 (1H, s, 4-CH) 7.3 and 7.5 (2×1H, s, 5-CH and 13-CH), 7.8, 7.83, 8.08, 8.12 (4H, 2-phenylene), 3.85 (3H, s, 8-OCH) 2.1 (3H, s, 11-$CH_3$).

Example 2

Substance 2

2-ethoxycarbonylmethyl-maduraphthalazine (10,12,15,16-tetrahydroxy-8-methoxy-2-ethoxycarbonyl-methyl-11-methyl-1,9,14-trioxo-1,2,6,7,9,14-hexahydro-naphthaceno-[1,2-g]-phthalazine), formula I wherein $R^1$=$CH_2COOC_2H_5$, $R^2$, $R^3$=H, $C_{30}H_{24}N_2O_{10}$(572.53).

A mixture of 1 g maduranic acid (97 percent) (2 mmoles) and 400 mg ethyl hydrazinoacetate hydrochloride (2.5 mmoles) was boiled in 20 ml glacial acetic acid with stirring for 2 hours. After filtration under suction, the product was well washed with water and glacial acetic acid and was recrystallised from glacial acetic acid. Light red crystals, m.p. 324–325° C. (decomposition). Yield: 622 mg (54% theoretical). Purity as determined by HPLC (Nucleosil RP18, acetonitrile/water (3:2)): 98.14%, t=10.45 min, DC (Merck Alufolie Si 60): butyl acetate/glacial acetic acid (4:1): $R_f$=0.87, MS FAB (3NBA) $[M+H]^+$: mass number found=573.1, $^1H$ NMR (DMSO-$D_6$) d(ppm): 14.07, 13.56, 12.77, 11.18 (4×H, s, 10, 12, 15 and 16-OH) 8.50 (1H, s, 4-CH), 7.40 and 7.28 (2H, s, 5-CH and 13-CH), 4.97 (2H, s, NCH$_2$) 4.15–4.25 (2H, q, CH$_2$ of ethyl), 3.81 (3H, s, 8-OCH$_3$) 2.08 (3H, s, 10-CH$_3$), 1.20–1.268 (3H, t, CH$_3$ of ethyl).

Example 3

Substance 3

2-carboxymethyl-maduraphthalazine (10,12, 15,16-tetrahydroxy-8-methoxy-2-carboxynmethyl-11-methyl-1,9,14-trioxo-1,2,6,7,9,14-hexahydro-naphthaceno-[1,2-g]-phthalazine), formula I wherein R$^1$=CH$_2$COOH, R$^2$, R$^3$=H, C$_{28}$H$_{20}$N$_2$O$_{10}$ (544.47).

570 mg (1 mmole) 2-carbethoxymethyl-maduraphthalazine (substance 2) were allowed to stand for 1 day in 35 ml of 2M caustic soda solution. The product was subsequently acidified with 2M hydrochloric acid. The red crystals obtained were purified by recrystallisation or by boiling in glacial acetic acid or by dissolution in tetrahydrofuran and precipitation with petroleum ether m.p. 234–236° C. (decomposition), yield: 322 mg (59% theoretical). Purity as determined by HPLC (Nucleosil RP18, acetonitrile/water (3:2), 99.8% t=0.87 minutes, DC (Merck Alufolie Si 60): butyl acetate/glacial acetic acid (4:1): R$_f$=0.31, MS FAB (3NBA) [M+H]$^+$: mass number found=545.0. $^1$H NMR (CDCl$_3$): d (ppm): 14.0, 13.5, 12.8, 11.2 (4H, s, 10,12,15 and 16-OH) 8.42 (1H, s, 4-CH), 7.2 and 7.3 (2H, s, 5-CH and 13-CH), 3.9 (3H, s, 7-OCH$_3$) 2.9 and 2.5 (2×2H, s, 6- and 7-CH$_2$), 2.1 (3H, s, 10-CH$_3$), $^{13}$C NMR (CDCl$_3$) 28 C atoms; d (ppm): 187.66 and 185.54 (quinone group), 169.0 (2-COOH), 61.04 (OCH$_3$), 52.30 (NCH$_2$), 29.21 and 22.21 (6- and 7-CH$_2$), 8.17 (11-CH$_3$). $^{13}$C NMR DEPT 135: d (ppm): 139.44 (CH=N) 114.19, 106.06 (2×ArH), 60.79 (8-OCH$_3$), 52.04 (NCH$_2$), 29.05, 21.96 (2×CH$_2$), 7.92 (11-CH$_3$).

A water-soluble trialkylammonium salt, for example a triethylammonium salt or an N-methyl-D-glucammonium salt, could be obtained from substance 3 by the addition of an amine, for example triethylamine or N-methyl-D-glucamine, in a suitable solvent, for example tetrahydrofuran.

Example 4

Substance 4

2-(D,L-a-carboxypropyl)-maduraphthalazine (10,12,15, 16-tetrahydroxy-8-methoxy-2-(D,L-a-carboxypropyl-11-methyl-1,9,14-trioxo-1,2,6,7,9,14-hexahydro-naphthaceno-[1,2-g]-phthalazine), formula I wherein R$^1$-50 D,L-a-carboxy-propyl, R$^2$, R$^3$=H, C$_{30}$H$_{24}$N$_2$O$_{10}$(572.15).

A mixture of 2 g (4.1 mmoles) madurahydroxylactone and 0.52 g (4.4 mmoles) D,L-a-hydrazinobutyric acid was boiled in 50 ml glacial acetic acid for 2 hours under reflux. After standing overnight, the dark red crystals were filtered off under suction, washed with ether and recrystallised from glacial acetic acid. Yield 1.8 g (76% theoretical), m.p. 225–230° C. (decomposition), purity as determined by HPLC (RP18 Eurospher 100 C7, acetonitrile/water (3:2)+ 0.05 percent trifluoroacetic acid): 99.6%, t=13.3 min, DC (Merck Alufolie Si 60): butyl acetate/glacial acetic acid (4:1): R$_f$=0.79, MS FAB (3NBA) [M+H]$^+$: mass number found=573.4, $^1$H NMR (DMSO-D6) d (ppm): 14.1, 13.6, 12.9, 11.3 (4H, s, 10, 12, 15 and 16-OH) 8.5 (1H, s, 4-CH), 7.2 and 7.4 (2H, s, 5-CH and 13-CH), 5.3 (1H, d, NCH), 3.9 (3H, s, 7-OCH$_3$), 2.0 (3H, s, 10CH$_3$), 0.9 (3H, s, CH$_3$aliph.). $^{13}$C NMR (DMSO-D6) Dept 135: d (ppm): 29.48, 22.43, 22.22 (3×CH$_2$).

The abbreviations used in the examples have the following meanings

DC - thin layer chromatography

THF - tetrahydrofuran

HPLC - high performance liquid chromatography min - minutes m.p. - melting point MS - mass spectrometry NMR - nuclear magnetic resonance

TABLE

Effectiveness of maduraphthalazine derivatives against various gram-positve bacterial strains

| Substance | MIC (mg/ml) Staphylococcus aureus | | | NCTC | Staphylococcus epidermidis | | Enterococcus faecium |
|---|---|---|---|---|---|---|---|
| | 8325-4[a] | 108/83[b] | 134/94[c] | 6571 | CCM 2124 | 70/90 | 64/3 |
| 1. | 0.5 | 0.25 | 0.5 | <0.125 | <0.125 | 0.5 | 0.5 |
| 3. | 0.063 | 0.063 | 0.25 | <0.125 | <0.125 | 2 | 0.5 |
| 4. | 0.063 | 0.032 | 0.016 | | | | |
| vancomycin | 0.5 | 0.5 | 0.5 | | 0.5 | 1024 | <0.25 |
| teicoplanin | 0.5 | 0.5 | 0.5 | | 0.5 | 256 | <0.25 |
| ciprofloxacin | 0.25 | 0.25 | 16.0 | | 0.25 | 1 | <0.25 |

[a] a sensitive Staphylococcus aureus strain, representative of the species
[b] "old" MRSA (without quinolone-resistance)
[c] "new" MRSA (with quinoline-resistance)

What is claimed is:

1. A polycyclic phthalazine compound corresponding to the formula:

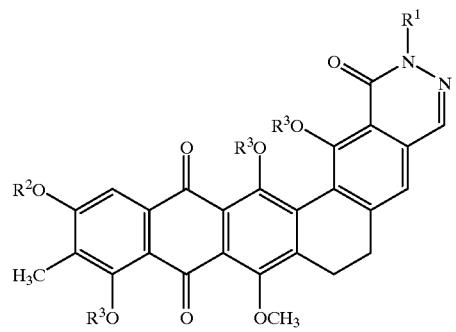

wherein

R$^1$ represents a carboxyalkyl or carboxyaryl group;

R$^2$ and R$^3$ independently represent hydrogen or an acyl group, or a salt, ester or amide thereof;

with the proviso that $R^1$ is other than a carboxyphenyl or substituted carboxyphenyl group when $R^3$ represents a $C_{1-8}$alkanoyl group.

2. A compound according to claim 1, wherein $R^1$ represents a group corresponding to the formula $-(CR^4R^5)_n-$COY or

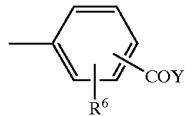

wherein $R^4$ and $R^5$ represent H, alkyl, aryl or substituted aryl;

n is an integer from 1 to 4;

$R^6$ represents H, alkyl, OH or alkoxy, and

Y represents $OR^7$ wherein $R^7$ represents H, alkyl, aryl, substituted aryl, an alkali metal ion or an ammonium ion, or Y represents $NR^8R^9$, wherein $R^8$ and $R^9$ independently represent H, alkyl, aryl, or substituted aryl or aralkyl.

3. A compound according to claim 1, wherein $R^1$ represents carboxy-$C_{1-4}$alkyl, $C_{1-4}$alkoxycarbonyl-$C_{1-4}$alkyl or carboxyphenyl, and $R^2$ and $R^3$ represent hydrogen.

4. A compound according to claim 3, in salt form.

5. A compound according to claim 3, in free acid form.

6. A compound according to claim 1, in salt form.

7. A compound according to claim 1, in free acid form.

8. A compound according to claim 2, wherein $R^7$ represents a trialkylammonium ion or a N-methyl-D-glucammonium ion.

9. A compound according to claim 1, wherein said compound is 2-carboxymethylmaduraphthalazine or a salt thereof.

10. A pharmaceutical composition comprising an effective antibacterial amount of a compound according to claim 1, and at least one pharmaceutical carrier or adjuvant.

11. A method of preparing a pharmaceutical composition comprising admixing an effective antibacterial amount of a compound according to claim 1, with at least one pharmaceutical carrier or adjuvant.

12. A method of treating a bacterial infection in a patient, said method comprising administering to said patient an effective antibacterial amount of a compound according to claim 1.

* * * * *